US012227724B2

(12) United States Patent
Yamanaka (10) Patent No.: US 12,227,724 B2
(45) Date of Patent: Feb. 18, 2025

(54) CELL CULTURE CHIP AND CELL CULTURE METHOD USING THE SAME

(71) Applicant: Ushio Denki Kabushiki Kaisha, Tokyo (JP)

(72) Inventor: Makoto Yamanaka, Tokyo (JP)

(73) Assignee: Ushio Denki Kabushiki Kaisha, Tokyo (JP)

(*) Notice: Subject to any disclaimer, the term of this patent is extended or adjusted under 35 U.S.C. 154(b) by 909 days.

(21) Appl. No.: 17/265,798

(22) PCT Filed: Jul. 2, 2019

(86) PCT No.: PCT/JP2019/026244
§ 371 (c)(1),
(2) Date: Feb. 3, 2021

(87) PCT Pub. No.: WO2020/039756
PCT Pub. Date: Feb. 27, 2020

(65) Prior Publication Data
US 2021/0238521 A1    Aug. 5, 2021

(30) Foreign Application Priority Data

Aug. 21, 2018  (JP) .................................. 2018-154791

(51) Int. Cl.
*C12M 1/00*   (2006.01)
*C12M 1/32*   (2006.01)

(52) U.S. Cl.
CPC ............ *C12M 23/12* (2013.01); *C12M 23/34* (2013.01)

(58) Field of Classification Search
CPC ....... C12M 23/12; C12M 23/34; C12M 23/16
See application file for complete search history.

(56) References Cited

U.S. PATENT DOCUMENTS 7,186,548 B2    3/2007  Li
7,374,906 B2*   5/2008  Kirk ...................... B82Y 15/00
                                                    435/287.8
(Continued)

FOREIGN PATENT DOCUMENTS

CN    105324478 A    2/2016
JP    2007-510429 A  4/2007
(Continued)

OTHER PUBLICATIONS

International Search Report for PCT/JP2019/026244 Mailded on Sep. 24, 2019, Including Written Opinion.
(Continued)

*Primary Examiner* — Liban M Hassan
(74) *Attorney, Agent, or Firm* — Yoshida & Associates LLC; Kenichiro Yoshida (57) ABSTRACT

A cell culture chip that enables observation of interactions between cells with a direction without additionally using a driving mechanism is provided.
A cell culture chip includes a first culture chamber capable of culturing a cell; a second culture chamber capable of culturing a cell independently from the first culture chamber; a first well connected to the first culture chamber and capable of storing a liquid; a second well connected to the second culture chamber and being capable of storing a liquid; and a connecting portion that, when a liquid level of a first liquid stored in the first well reaches a predetermined height position or higher, allows the first liquid to flow from the first well into the second well.

4 Claims, 9 Drawing Sheets

(56) References Cited

U.S. PATENT DOCUMENTS

| | | | |
|---|---|---|---|
| 2005/0101010 A1 | 5/2005 | Li | |
| 2008/0213855 A1* | 9/2008 | Firth | C12Q 1/02 435/173.6 |
| 2016/0369224 A1 | 12/2016 | Shimasaki et al. | |
| 2019/0046978 A1 | 2/2019 | Shimasaki et al. | |

FOREIGN PATENT DOCUMENTS

| | | | | |
|---|---|---|---|---|
| JP | 2004-000163 A | 1/2024 | | |
| WO | 1993/022418 A | 11/1993 | | |
| WO | 2016/154361 A | 9/2016 | | |
| WO | 2017/138648 A1 | 8/2017 | | |
| WO | WO-2017154880 A1 * | 9/2017 | | C12M 1/00 |
| WO | 2018/009870 A1 | 1/2018 | | |

OTHER PUBLICATIONS

Chinese Office Action for CN 201980053903.7, Which Corresponds to U.S. Appl. No. 17/265,798, dated Aug. 19, 2023.
Supplemental European Search Report for EP 19851192.5, Which Corresponds to U.S. Appl. No. 17/265,798, dated May 25, 2022.

* cited by examiner

CELL CULTURE CHIP AND CELL CULTURE METHOD USING THE SAME

TECHNICAL FIELD

The present invention relates to cell culture chips, and particularly relates to a cell culture chip used for independently culturing a plurality of cells. The present invention also relates to a cell culture method using the cell culture chip.

BACKGROUND ART

Figure 10:
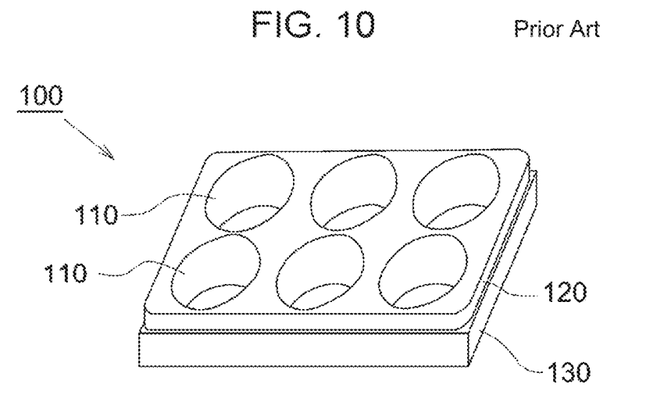
FIG. 10 is a perspective view schematically illustrating an example of a structure of a multi-well cell culture chip of related art.
Figure 11:
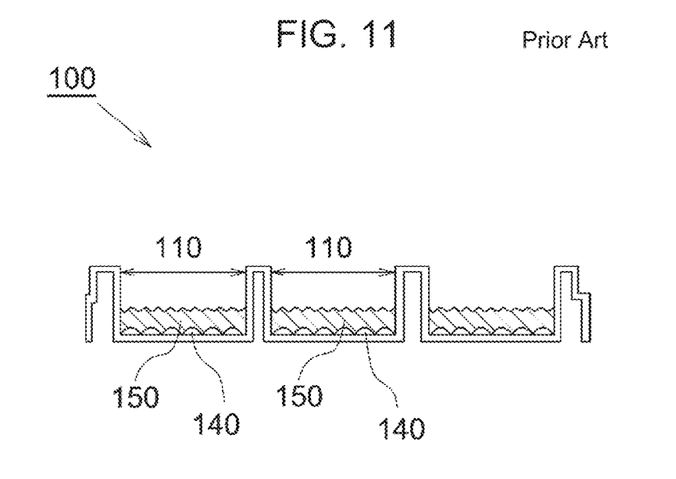
FIG. 11 is a sectional view schematically illustrating the structure of the cell culture chip illustrated in FIG. 10.

Conventionally, a cell culture chip including a plurality of wells has been known for the purpose of simultaneously culturing multiple cells. Such a cell culture chip may be referred to as a "multi-well" culture chip. FIGS. 10 and 11 illustrate a structure of a multi-well cell culture chip of related prior art. FIG. 10 corresponds to a perspective view, and FIG. 11 corresponds to a sectional view.

A cell culture chip 100 illustrated in FIG. 10 includes six wells 110 having the same shape. More specifically, the cell culture chip 100 includes an upper tray 120 having through holes and a lower tray 130 disposed in contact with the upper tray 120. A surface of the lower tray 130 and the through holes of the upper tray 120 define the wells 110.

As illustrated in FIG. 11, cells 140 are placed on a bottom surface of each well 110, and a culture solution 150 is added to cover the cells 140.

However, in the configuration of the cell culture chip 100 illustrated in FIG. 10, since the wells 110 are independent from one another, it is not possible to use the cell culture chip 100 for the purpose of examining interactions between cells 140 placed in the respective wells 110. In such a viewpoint, for example, PTL 1 listed below discloses a cell culture chip in which different wells can store a common culture solution (culture medium).

CITATION LIST

Patent Literature

PTL 1: Japanese Laid-open Patent Publication No. 2007-510429

SUMMARY OF INVENTION

Technical Problem

Figure 12:
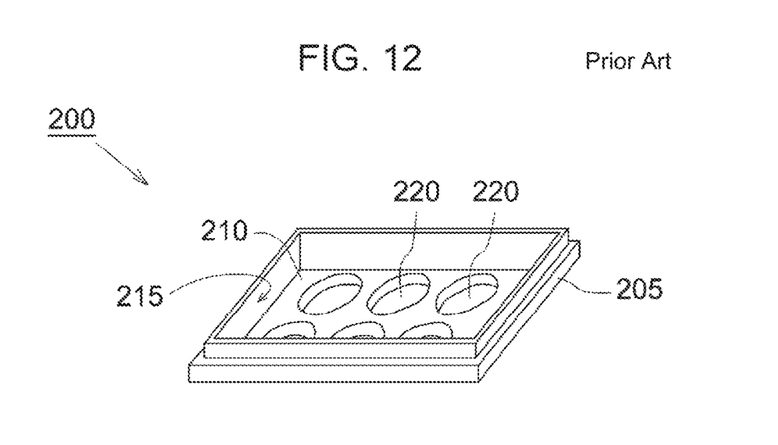
FIG. 12 is a perspective view schematically illustrating an example of a structure of a multi-well cell culture chip of related art.
Figure 13:
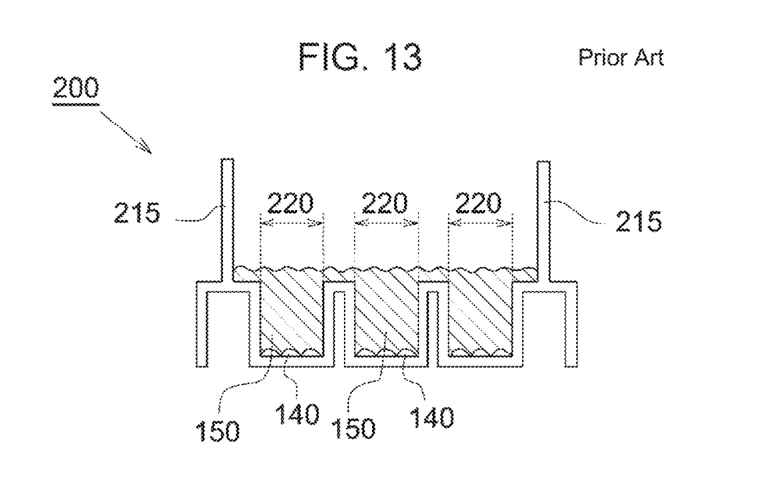
FIG. 13 is a sectional view schematically illustrating the structure of the cell culture chip illustrated in FIG. 12.

FIGS. 12 and 13 illustrate an example of a prior-art structure of a multi-well cell culture chip disclosed in PTL 1. FIG. 12 corresponds to a perspective view, and FIG. 13 corresponds to a sectional view.

A multi-well cell culture chip 200 illustrated in FIG. 12 includes a main body 205 and an outer wall 215 disposed on an upper surface 210 of the main body 205. Six recesses are provided at predetermined positions of the upper surface 210 of the main body 205 to define wells 220.

When cells are cultured, cells 140 are placed on a bottom surface of each well 220, and a culture solution 150 is added to cover the cells 140. Here, as illustrated in FIG. 13, the culture solution 150 is supplied to the cell culture chip 200 until the liquid level of the culture solution 150 reaches a position exceeding a top plane of each well 220. At this time, the wells 220 communicate with one another via the culture solution 150. Thus, it is possible to observe the influence of a physiologically active substance released from a cell 140 cultured in a certain well 220 on another cell 140 cultured in another well 220.

The inventors have studied functions and effects of ES/iPS cells by simulating an environment closer to that in a living body. In the course of such studies, when the simulation of the environment close to that in the living body is considered, it has been found that there is a need to simultaneously culture a certain cell A and another cell B, and observe the influence of a physiologically active substance Xa released from the cell A on the cell B in a state in which the influence of a physiologically active substance Xb released from the cell B on the cell A is eliminated.

However, in the case of the cell culture chip 200 illustrated in FIGS. 12 and 13, although it is possible to observe the interaction between the cells 140 cultured in all the wells 220, it is not possible to use the cell culture chip 200 for the purpose of observing the influence from a specific certain cell to another specific certain cell.

As another method, a method of culturing cells while forcibly causing a culture solution to flow in one direction using a driving mechanism such as a pump can be considered. However, if a driving mechanism such as a pump is used when cells are cultured, there are problems in that the size of the chip markedly increases and the handling of a power source becomes complicated. As long as the size of the chip can be reduced, multiple cells can be cultured within the same area, thereby markedly increasing the efficiency of the study.

In view of the above problems, an object of the present invention is to provide a cell culture chip and a cell culture method that enables observation of interactions between cells with a direction without additionally using a driving mechanism.

Solution to Problem

A cell culture chip according to the present invention includes
 a first culture chamber capable of culturing a cell;
 a second culture chamber disposed at a position separated from the first culture chamber and being capable of culturing a cell independently from the first culture chamber;
 a first well connected to the first culture chamber and capable of storing a liquid;
 a second well connected to the second culture chamber and capable of storing a liquid; and
 a connecting portion that, when a liquid level of a first liquid stored in the first well reaches a predetermined height position or higher, allows the first liquid to flow from the first well into the second well.

According to the cell culture chip, the first liquid can flow into the second well from the first well only by controlling the solution amount of the culture solution. Since the first liquid is stored in the first well connected to the first culture chamber, the first liquid contains a physiologically active substance (hereinafter, referred to as a "first physiologically active substance") released from the cell (hereinafter referred to as a "first cell") cultured in the first culture chamber. Thus, when the first liquid flows into the second culture chamber through the second well, the first physiologically active substance contained in the first liquid comes into contact with a cell (hereinafter, referred to as a "second cell") cultured in the second culture chamber. Consequently, the influence of the first physiologically active substance on the second cell can be observed.

In contrast, according to the cell culture chip, the culture solution in contact with the second culture chamber does not flow to the first culture chamber side. Consequently, the physiologically active substance (hereinafter, referred to as a "second physiologically active substance") released from the second cell can be prevented from exerting an influence on the first cell.

With the cell culture chip, the first physiologically active substance can be brought into contact with the second cell only by adjusting the supply amount of the culture solution. Thus, it is not necessary to additionally provide a driving mechanism such as a pump. Consequently, the size of the cell culture chip can be reduced.

In the cell culture chip,
the first well and the second well may be adjacent to each other via a partition wall, and
the connecting portion may be constituted by the partition wall.

In this case, the partition wall may include a cutout portion having a bottom surface whose height position varies in accordance with a place of the bottom surface.

According to the above configuration, it is possible to freely adjust the speed at which the first liquid flows into the second well and the amount of the culture solution supplied to cause the first liquid to flow into the second well in accordance with the shape of the cutout portion.

In the cell culture chip,
the first well and the second well may be adjacent to each other via a gutter-shaped flow path, and
the connecting portion may be constituted by the gutter-shaped flow path.

In the cell culture chip,
a bottom surface of the first well and a bottom surface of the first culture chamber may be constituted by a common surface, and
a length of the first culture chamber in a vertical direction may be shorter than a length from the bottom surface of the first well to the predetermined height position.

According to this configuration, since the bottom surface of the first well and the bottom surface of the first culture chamber are common, the cell culture chip can be manufactured by a simple method.

The cell culture chip may include
a third well connected to the first culture chamber at a position opposite to the first well; and
a fourth well connected to the second culture chamber at a position opposite to the second well.

According to the above configuration, the first liquid stored in the first well is pushed out to the second well side by supplying the culture solution from the third well side. Moreover, the liquid flowing through the second culture chamber can be taken out from the fourth well side.

In the above-described configuration, a bottom surface of the first well, a bottom surface of the first culture chamber, a bottom surface of the third well, a bottom surface of the second well, a bottom surface of the second culture chamber, and a bottom surface of the fourth well may be all constituted by a common surface.

A cell culture method according to the present invention includes
a step (a) of culturing a cell independently in each of the first culture chamber and the second culture chamber; and
a step (b) of supplying a culture solution through the first culture chamber to raise a height position of the liquid level of the first liquid stored in the first well.

In the step (b), an inflow amount of the culture solution is adjusted such that the first liquid flows into the second culture chamber through the connecting portion and the second well.

In the cell culture method,
the cell culture chip may include a third well connected to the first culture chamber at a position opposite to the first well, and
the step (b) may be a step of supplying the culture solution from the third well.

Advantageous Effects of Invention

According to the present invention, a cell culture chip and a cell culture method that enables observation of interactions between cells with a direction without additionally using a driving mechanism are implemented.

BRIEF DESCRIPTION OF DRAWINGS

FIG. 8A (a) is a sectional view of the cell culture chip taken along line X1-X1 in FIG. 2, schematically illustrating an initial state of a step (a) of a predetermined method of using the cell culture chip.

FIG. 8A (b) is a sectional view of the cell culture chip taken along line X1-X1 in FIG. 2, schematically illustrating a next state of the step (a) of the predetermined method of using the cell culture chip.

FIG. 8A (c) is a sectional view of the cell culture chip taken along line X1-X1 in FIG. 2, schematically illustrating a yet next state of the step (a) of the predetermined method of using the cell culture chip.

FIG. 8B (a) is a sectional view of the cell culture chip taken along line X1-X1 in FIG. 2, schematically illustrating an initial state of a step (b) of the predetermined method of using the cell culture chip.

FIG. 8B (b) is a sectional view of the cell culture chip taken along line X1-X1 in FIG. 2, schematically illustrating a next state of the step (b) of the predetermined method of using the cell culture chip.

FIG. 8B (c) is a sectional view of the cell culture chip taken along line X1-X1 in FIG. 2, schematically illustrating a yet next state of the step (b) of the predetermined method of using the cell culture chip.

DESCRIPTION OF EMBODIMENTS

A cell culture chip and a cell culture method according to the present invention will be described with reference to the drawings. It should be noted that the following drawings are merely schematically illustrated. That is, the dimensional ratios on the drawings and the actual dimensional ratios do not necessarily coincide with each other, and the dimensional ratios do not necessarily coincide with each other between the drawings.

[Structure]

Figure 1:
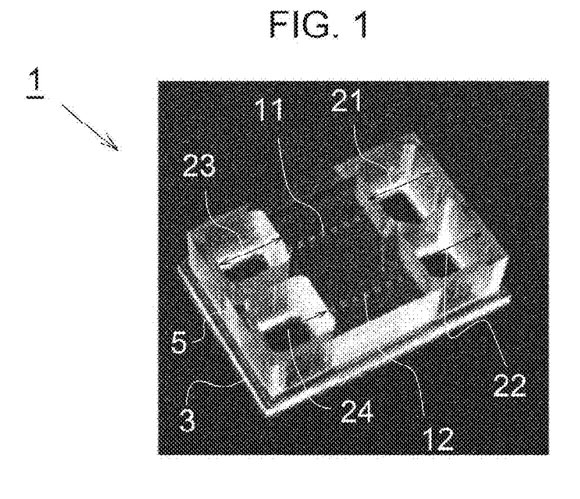
FIG. 1 is a photograph indicating a structure of an embodiment of a cell culture chip.
Figure 2:
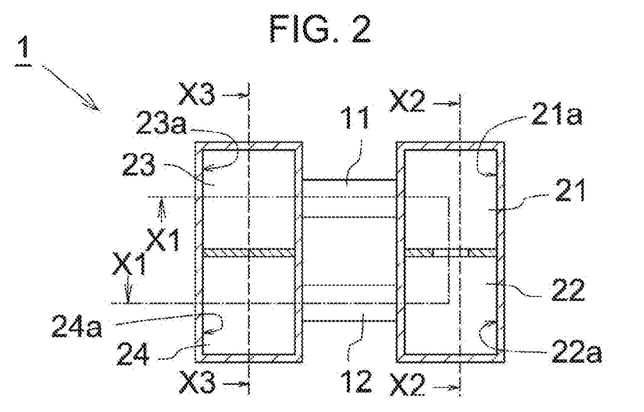
FIG. 2 is a plan view schematically illustrating the structure of the cell culture chip illustrated in FIG. 1.
Figure 3:
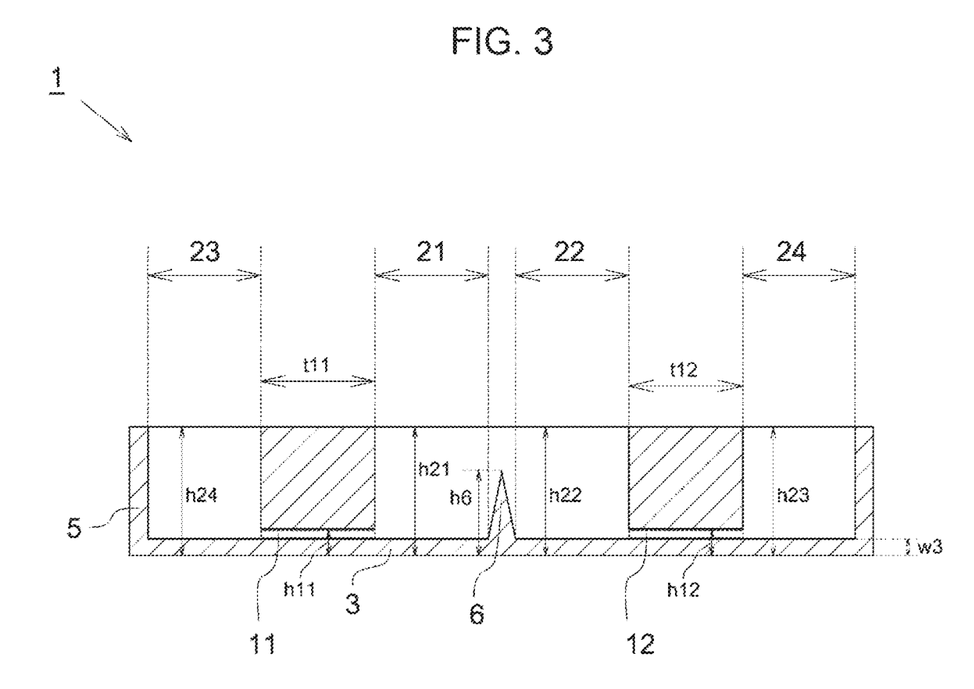
FIG. 3 is a composed sectional view of sectional views taken along line X1-X1 in FIG. 2.
Figure 4:
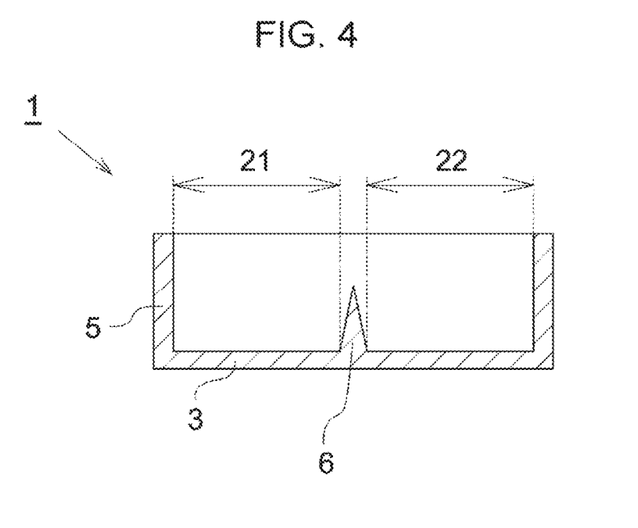
FIG. 4 is a sectional view taken along line X2-X2 in FIG. 2.
Figure 5:
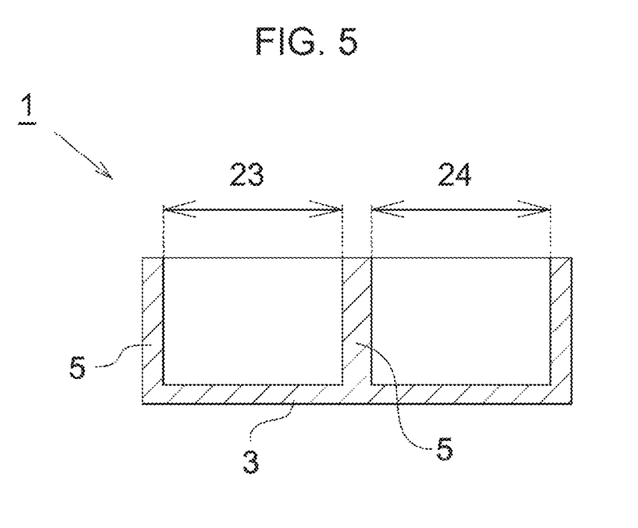
FIG. 5 is a sectional view taken along line X3-X3 in FIG. 2.

FIG. 1 is a photograph indicating a structure of an embodiment of a cell culture chip. FIG. 2 is a plan view schematically illustrating the structure of the cell culture chip 1 illustrated in FIG. 1. FIG. 3 is a schematic sectional view when the cell culture chip 1 is cut along line X1-X1 in FIG. 2. FIG. 4 is a schematic sectional view when the cell culture chip 1 is cut along line X2-X2 in FIG. 2. FIG. 5 is a schematic sectional view when the cell culture chip 1 is cut along line X3-X3 in FIG. 2.

The cell culture chip 1 illustrated in FIGS. 1 to 5 includes a first culture chamber 11, a second culture chamber 12, a first well 21, a second well 22, a third well 23, and a fourth well 24. Each of the first culture chamber 11, the second culture chamber 12, the first well 21, the second well 22, the third well 23, and the fourth well 24 constitutes a cylindrical or tubular space enclosed by a wall portion. The first culture chamber 11 and the second culture chamber 12 constitute spaces for culturing cells.

In this embodiment, the cell culture chip 1 includes a bottom portion 3 and a main body 5. The main body 5 has four through holes, and one plane of each through hole is in contact with the bottom portion 3 to define each of the wells (21 to 24). Moreover, the main body 5 has a pair of thin tubular recesses in a surface of the main body 5 on the side near the bottom portion 3. Regions between the recesses and the bottom portion 3 define the culture chambers (11 and 12).

One end of the first culture chamber 11 is connected to the third well 23, and the other end of the first culture chamber 11 is connected to the first well 21. One end of the second culture chamber 12 is connected to the second well 22, and the other end of the second culture chamber 12 is connected to the fourth well 24.

As illustrated in FIGS. 1 to 4, the first culture chamber 11 and the second culture chamber 12 are disposed at positions separated from each other. In addition, a partition wall 6 is formed between the first well 21 and the second well 22. In the present embodiment, the partition wall 6 constitutes a "connecting portion". In contrast, as illustrated in FIG. 5, the third well 23 and the fourth well 24 are completely separated by a wall of the main body 5.

Figure 6:
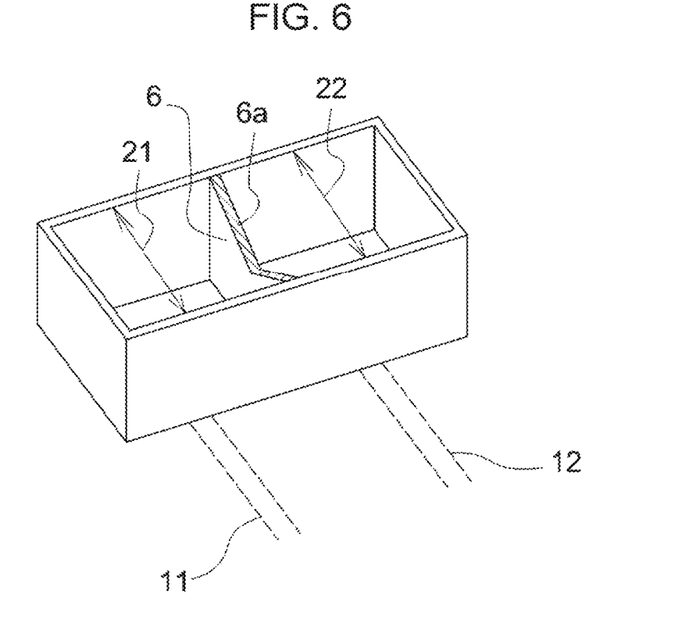
FIG. 6 is a schematic perspective view illustrating portions corresponding to a first well and a second well.
Figure 7:
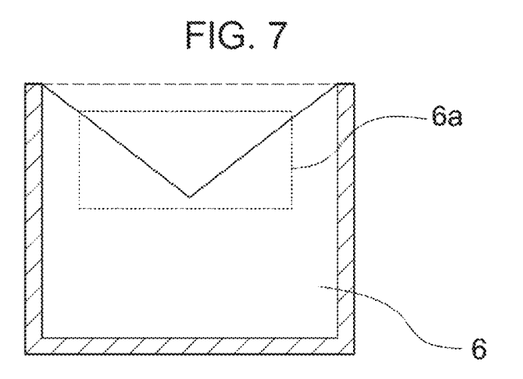
FIG. 7 is a schematic plan view of a partition wall when viewed in a direction from the first well toward the second well in FIG. 6.

FIG. 6 is a schematic perspective view illustrating only portions corresponding to the first well 21 and the second well 22 extracted from the cell culture chip 1. The partition wall 6 is provided between the first well 21 and the second well 22. In the present embodiment, the partition wall 6 has a cutout portion 6a having different heights in accordance with a position of the cutout portion 6a. FIG. 7 is a schematic plan view of the partition wall 6 when viewed in a direction from the first well 21 toward the second well 22.

A height h11 of the first culture chamber 11 is lower than a height h6 of the partition wall 6. Moreover, a height h21 of the first well 21 is higher than the height h6 of the partition wall 6.

An example of the dimensions is as follows. A height (thickness) w3 of the bottom portion 3 is about 1 mm, or preferably 100 μm or more and 2 mm or less. The height h21 of the first well 21, a height h22 of the second well 22, a height h23 of the third well 23, and a height h24 of the fourth well 24 each are about 5 mm. The height h11 of the first culture chamber 11 and a height h12 of the second culture chamber 12 each are about 1.4 mm. The height h6 of the partition wall 6 is about 3 mm. The size of a plane (opening plane) of each of the first well 21, the second well 22, the third well 23, and the fourth well 24 in a direction parallel to the surface of the bottom portion 3 is about 3.5 mm square. The distance from an end surface 23a of the third well 23 located opposite to the first well 21 to an end surface 21a of the first well 21 located opposite to the third well 23 is about 12.5 mm. The distance from an end surface 22a of the second well 22 located opposite to the fourth well 24 to an end surface 24a of the fourth well 24 located opposite to the second well 22 is about 12.5 mm. A length t11 of the first culture chamber 11 in the longitudinal direction and a length t12 of the second culture chamber 12 in the longitudinal direction each are about 5.5 mm.

Both the bottom portion 3 and the main body 5 constituting the cell culture chip 1 are preferably made of a transparent material. Thus, the cells cultured in the first culture chamber 11 and the second culture chamber 12 can be visually recognized from the outside of the cell culture chip 1. In addition, the bottom portion 3 and the main body 5 constituting the cell culture chip 1 are preferably made of a material applicable to injection molding.

[Method of Use]

Hereinafter, an example of a method of using the above-described cell culture chip 1 will be described with reference to FIG. 8A and FIG. 8B.

As illustrated in 8A(a), a culture solution 42 containing a predetermined cell 41 is supplied from the third well 23 side, and a culture solution 52 containing a predetermined cell 51 is supplied from the fourth well 24 side. It should be noted that the cell 51 is a target cell for evaluation of the influence of a physiologically active substance released from the cell 41. As an example, the cell 41 may be a liver cell and the cell 51 may be a kidney cell. As another example, the cell 41 may be a heart cell and the cell 51 may be a kidney cell. The reverse of such an example is also possible.

To supply the culture solutions (42 and 52), for example, a micropipette can be used. The culture solution 42 supplied from the third well 23 side reaches the inside of the first well 21 through the first culture chamber 11. The culture solution 52 supplied from the fourth well 24 side reaches the inside of the second well 22 through the second culture chamber 12.

At this time, the inflow amount of the culture solution 42 is set to an amount within a range in which the culture solution 42 does not flow over the partition wall 6 when the culture solution 42 reaches the inside of the first well 21. Likewise, the inflow amount of the culture solution 52 is set to an amount within a range in which the culture solution 52 does not flow over the partition wall 6 when the culture solution 52 reaches the inside of the second well 22.

Figure 8A:
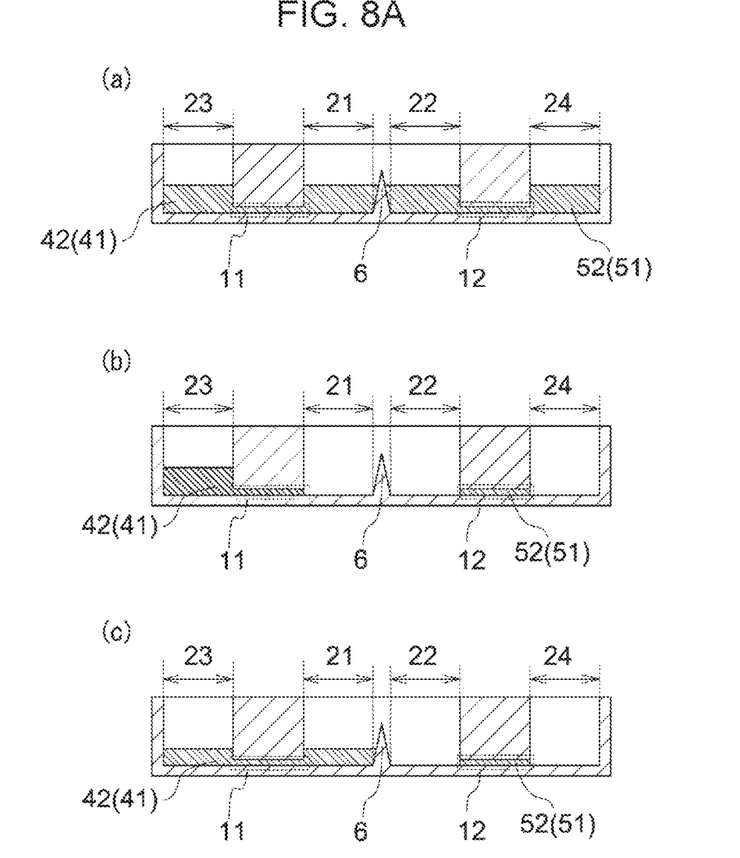
Figure 8B:
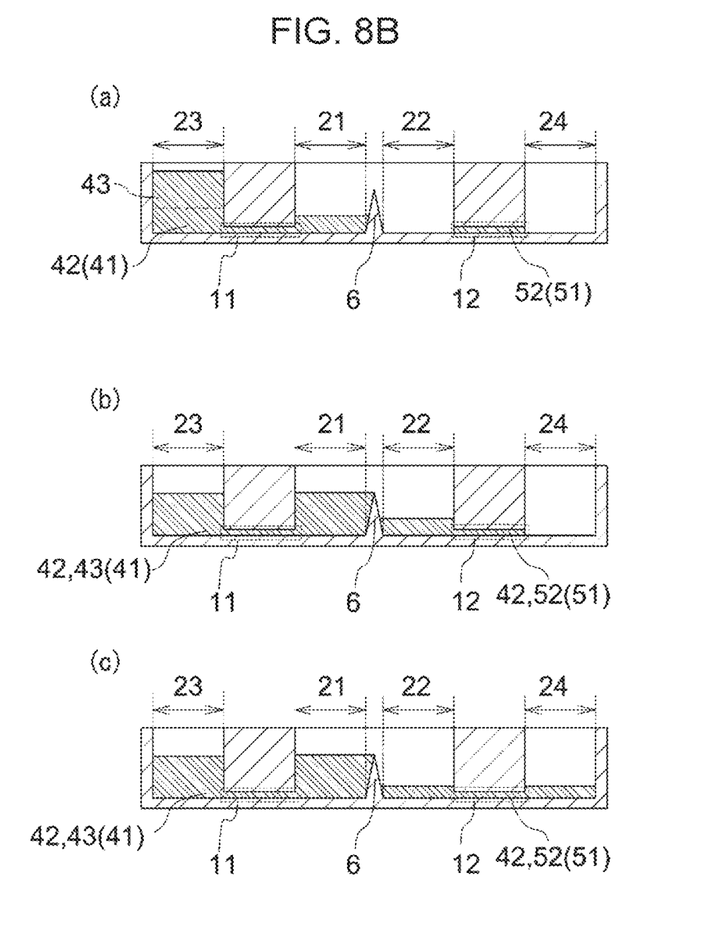

Next, as illustrated in FIG. 8A(b), the culture solution 42 stored in the first well 21 and the culture solution 52 stored in the second well 22 and the fourth well 24 are removed. A micropipette can be also used to remove the culture solutions (42, 52). Thereafter, the culture solution 42 stored in the third well 23 flows to the first well 21 side, and the state illustrated in FIG. 8A(c) is obtained.

By this step, the culture solution 42 containing the cell 41 is held in the first culture chamber 11, and the culture solution 52 containing the cell 51 is held in the second culture chamber 12. That is, an environment in which the cell 41 is cultured in the first culture chamber 11 and the cell 51 is cultured in the second culture chamber 12 is formed. This step corresponds to a step (a).

By maintaining this state for a predetermined period of time, the cell 41 cultured in the first culture chamber 11 releases a physiologically active substance into the culture solution 42. Examples of the physiologically active substance include a cytokine, a hormone, a lipid, an extracellular matrix, a microRNA, an exosome, a nutrient, and a drug, which exhibit an endocrine action. If necessary, an amount of the culture solution 42 within a range in which the culture solution 42 stored in the first well 21 does not flow over the partition wall 6 may be additionally supplied from the third well 23 side.

After a predetermined period of time has elapsed, a culture solution 43 is supplied from the third well 23 side (FIG. 8B(a)). The culture solution 43 may be made of the same material as the material of the culture solution 42, or may be made of a material different from the material of the culture solution 42 as long as the material of the culture solution 43 does not exert an influence on the cell 41. The culture solution 42 corresponds to a "first liquid". Thus, the liquid level of the culture solution 42 stored in the first well 21 rises. The culture solution 43 is supplied by such an amount that the culture solution 42 can flow over the partition wall 6. Consequently, the culture solution 42 containing the physiologically active substance released from the cell 41 is supplied to the second culture chamber 12 via the second well 22 (FIG. 8B(b) and FIG. 8B(c)). This step corresponds to a step (b).

Then, the process waits for a predetermined period of time in the state of FIG. 8B(c). Accordingly, the physiologically active substance released from the cell 41 is held for a certain period of time in a state in contact with the cell 51 that has been cultured in the second culture chamber 12. Thus, it is possible to evaluate whether or not the physiologically active substance released from the cell 41 exerts an influence on the cell 51 and how the physiologically active substance has the influence on the cell 51.

As described above, according to the cell culture chip 1, the physiologically active substance released from the cell 41 can be brought into contact with the cell 51 only by adjusting the supply amount of the culture solution 43 supplied from the third well 23 side. Thus, it is not necessary to additionally provide a driving mechanism such as a pump. In addition, since the physiologically active substance released from the cell 51 does not act on the cell 41, it is possible to more accurately evaluate the influence of the physiologically active substance released from the cell 41 on the cell 51.

Other Embodiments

Other embodiments will be described below.

<1> The cell culture chip 1 of the above-described embodiment has the configuration in which the first well 21 and the second well 22 are separated by the partition wall 6, and the culture solution 42 flows from the first well 21 to the second well 22 side when the liquid level of the culture solution 42 exceeds the height of the partition wall 6. However, the cell culture chip 1 is not limited to such an embodiment. That is, instead of the partition wall 6, the cell culture chip 1 may be configured to include a connecting portion that allows the culture solution 42 to flow into the second well 22 from the first well 21 only when the liquid level of the culture solution 42 exceeds a predetermined height.

Figure 9:
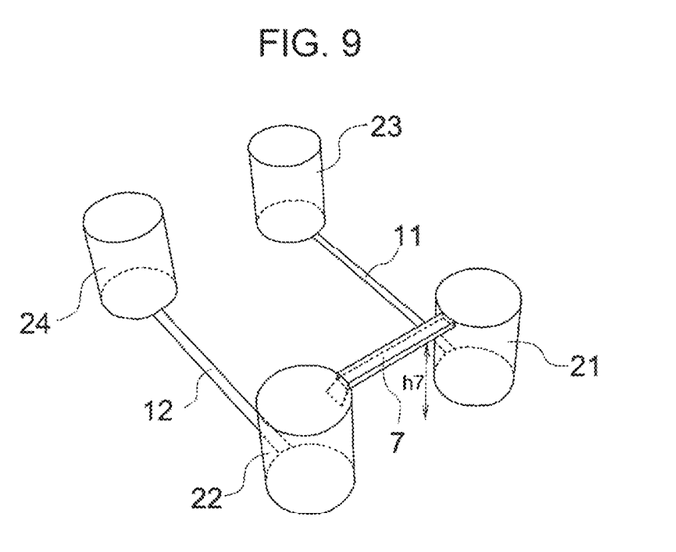
FIG. 9 is a perspective view schematically illustrating a structure of another embodiment of a cell culture chip.

As an example, as schematically illustrated in FIG. 9, the cell culture chip 1 may be configured to include a gutter-shaped flow path 7 that connects the first well 21 and the second well 22 to each other. The gutter-shaped flow path 7 guides the culture solution 42 to the second well 22 side only when the liquid level of the culture solution 42 stored in the first well 21 exceeds a height h7 of the gutter-shaped flow path 7. With this configuration as well, the physiologically active substance released from the cell 41 can be brought into contact with the cell 51 only by adjusting the supply amount of the culture solution 43 supplied from the third well 23 side.

As another example, the cell culture chip 1 may include a tube-shaped flow path that connects the first well 21 and the second well 22 to each other.

<2> The cell culture chip 1 may not necessarily include the third well 23 as long as the culture solution 42 (43) can be injected into the first culture chamber 11. Likewise, the cell culture chip 1 may not necessarily include the fourth well 24.

<3> In the above-described embodiment, the case where the cell culture chip 1 includes the two culture chambers (11 and 12) has been described. However, the cell culture chip 1 may include three or more culture chambers connected in series.

<4> In the above-described embodiment, the case where the wells (21, 22, 23, and 24) and the culture chambers (11 and 12) have a common bottom surface that is the upper surface of the bottom portion 3 has been described. This form is an example. However, it is preferable that the wells (21, 22, 23, and 24) and the culture chambers (11 and 12) have a common bottom surface in terms of facilitating the manufacturing process of the cell culture chip 1 and enabling the size of the cell culture chip 1 to be markedly reduced.

<5> In the above-described embodiment, the case where the partition wall 6 has the shape having the cutout portion 6a has been described. However, when the cell culture chip 1 includes the partition wall 6, the partition wall 6 does not necessarily have the shape having the cutout portion 6a as long as the height of the partition wall 6 is configured to be lower than the height of the other wall surfaces of the first well 21. When the cell culture chip 1 includes the partition wall 6 having the cutout portion 6a, it is possible to appropriately adjust the speed at which the culture solution 42 flows to the second culture chamber 12 side in accordance with the shape and height position of the cutout portion 6a.

REFERENCE SIGNS LIST

1: cell culture chip
3: bottom portion
5: main body
6: partition wall
6a: cutout portion of partition wall
7: gutter-shaped flow path
11: first culture chamber
12: second culture chamber
21: first well 21a: wall surface of first well
22: second well
22a: wall surface of second well
23: third well
23a: wall surface of third well
24: fourth well
24a: wall surface of fourth well
41: cell
42, 43: culture solution
51: cell
52: culture solution
100: cell culture chip of related art
110: well
120: upper tray
130: lower tray
140: cell
150: culture solution
200: cell culture chip of related art
205: main body
210: top surface of main body
215: outer wall
220: well

The invention claimed is:

1. A cell culture chip comprising:
a base plate;
a main body having tubular recesses and walls located above the base plate, the main body and the base plate together forming a first culture chamber, a second culture chamber, a first well, a second well, a third well, and a fourth well all for storing at least liquid; and
a connector having at most a second predetermined height located above the base plate between the first well and the second well;
wherein the first culture chamber and the second culture chamber are each one of the tubular recesses having a third predetermined height for culturing cells and located in the main body bellow the walls with a recess bottom surface which the base plate forms,
wherein the first well, the second well, the third well and the fourth well are each separately formed by the walls having a first predetermined height of the main body with a well bottom surface which the base plate forms,
Wherein one end of the first culture chamber is connected to the first well while the other end of the first culture chamber is connected to the third well, one end of the second culture chamber is connected to the second well while the other end of the second culture chamber is connected to the fourth well,
whereas at most the second predetermined height is shorter than the first predetermined height and taller than the third predetermined height so that the connector allows a flow of the liquid between the first well and the second well as the liquid accumulates in the first well over the connector.

2. The cell culture chip according to claim 1,
wherein the first well and the second well are adjacent to each other via a partition wall, and
wherein the connector is constituted by the partition wall.

3. The cell culture chip according to claim 2, wherein the partition wall includes a cutout portion whose height from a bottom surface is at most the second predetermined height but varies in accordance with a position of the cutout portion.

4. The cell culture chip according to claim 1, wherein a bottom surface of the first well, a bottom surface of the first culture chamber, a bottom surface of the third well, a bottom surface of the second well, a bottom surface of the second culture chamber, and a bottom surface of the fourth well are all constituted by a common surface.

* * * * *